United States Patent
Bernreuter

[11] Patent Number: 5,772,589
[45] Date of Patent: Jun. 30, 1998

[54] MEASUREMENT PROCESS FOR BLOOD GAS ANALYSIS SENSORS

[76] Inventor: Peter Bernreuter, Unterleinsied1 4, D-92289 Ursensollen, Germany

[21] Appl. No.: 716,321

[22] PCT Filed: Oct. 3, 1995

[86] PCT No.: PCT/EP95/03903

§ 371 Date: Nov. 19, 1996

§ 102(e) Date: Nov. 19, 1996

[87] PCT Pub. No.: WO96/11623

PCT Pub. Date: Apr. 25, 1996

[30] Foreign Application Priority Data

Feb. 13, 1995 [DE] Germany ............... 195 18 158.1
Apr. 4, 1995 [DE] Germany ............... 195 12 478.2

[51] Int. Cl.[6] ............................................. A61N 5/00
[52] U.S. Cl. ............................................ 600/323; 600/336
[58] Field of Search ........................... 128/632, 633

[56] References Cited

U.S. PATENT DOCUMENTS

| | | |
|---|---|---|
| 3,922,088 | 11/1975 | Lubbers et al. . |
| 4,114,604 | 9/1978 | Shaw et al. . |
| 5,057,695 | 10/1991 | Hirao et al. . |
| 5,078,136 | 1/1992 | Stone et al. ............... 128/633 |
| 5,190,040 | 3/1993 | Aoyagi ..................... 128/633 |
| 5,259,381 | 11/1993 | Cheung et al. ............ 128/633 |
| 5,278,627 | 1/1994 | Aoyagi et al. ............. 128/633 |
| 5,279,295 | 1/1994 | Martens et al. . |
| 5,284,137 | 2/1994 | Kessler et al. . |
| 5,421,329 | 6/1995 | Casciani et al. .......... 128/633 |
| 5,503,148 | 4/1996 | Pologe et al. ............. 128/633 |

FOREIGN PATENT DOCUMENTS

| | | |
|---|---|---|
| 0286142 | 10/1988 | European Pat. Off. . |
| 0335357 | 10/1989 | European Pat. Off. . |
| 4313011 | 10/1994 | Germany . |

Primary Examiner—William E. Kamm
Attorney, Agent, or Firm—Dennison, Meserole, Pollack & Scheiner

[57] ABSTRACT

This is a method for measuring oxygen saturation of arterial blood in tissue using at least two different wavelengths of light directed into the tissue and measuring the amount of radiation retained by the tissue and compensating the measurements for tissue haemoglobin content and skin pigmentation and pilosity and calibrating the equipment by obtaining measurements after the injection of a medical dye into the tissue.

3 Claims, 2 Drawing Sheets

MEASUREMENT PROCESS FOR BLOOD GAS ANALYSIS SENSORS

BACKGROUND OF THE INVENTION

The invention relates to a measuring process, the purpose of which is to increase the measuring accuracy of pulse oxymeters which are used in vive to ascertain oxygen saturation of arterial blood.

According to the current prior art pulse oxymeters function on the basis that at differing wavelengths blood attenuates light very differently depending upon the level of oxygenation. Pulse waves starting from the heart cause in the arterial blood vessel system a periodic fluctuation in the arterial blood content in the tissue. As a consequence, a periodic change in the light absorption (FIG. 4) can be registered between the light transmitter, whose radiation passes through the tissue, and the receivers, which are integrated in a pulse oxymetry sensor. The evaluation of the sensor signals is normally carried out at light wavelengths of 660 and 940 nm. It is possible to create a measured variable $\Omega$ (sometimes also referred to as R) which is obtained in the following manner or in a similar manner:

$$\Omega = \frac{\left(\frac{\text{Light intensity fluctuation at 660 nm}}{\text{Total light intensity at 660 nm}}\right)}{\left(\frac{\text{Light intensity fluctuation at 940 nm}}{\text{Total light intensity at 940 nm}}\right)} = \frac{\left(\frac{AC}{DC}\right)_{660_{nm}}}{\left(\frac{AC}{DC}\right)_{940_{nm}}} \approx \frac{\ln\left(\frac{I_{min}}{I_{max}}\right)_{660_{nm}}}{\ln\left(\frac{I_{min}}{I_{max}}\right)_{940_{nm}}}$$

The light intensities described in the formula represent the light intensities received in the receiver of the sensors used in pulse oxymetry. The measured variable $\Omega$ serves as a measurement for the oxygen saturation. The formation of a quotient in order to form the measured variable is intended to compensate any possible influences the haemoglobin content of the tissue, the pigmentation of the skin or the pilosity may have on the measurement of the oxygen saturation of arterial blood. (See also "Biomedizinische Technic" [Biomedical Technology] Volume 33, Supplementary volume 3, page 6 ff.: "Pulse oxymetrie: Stand und Entwicklung der Technik" [Pulse oxymetry; Status and development of the technology"; Volume 35, Supplementary volume 1, page 38 ff. "Pulsoxymetrie" [Pulse oxymetry] by K Forstner Institute for Biomedical Technology, Stuttgart). The influences of blood perfusion in the tissue, the pigmentation and pilosity are not taken into consideration in this measuring process.

When measuring oxygen saturation of arterial blood in the tissue in a range of 70 to 100% using light of a wavelength 940 nm and 660 nm this also produces sufficiently accurate measured values. However, in order to measure lower oxygen saturation of arterial blood it is necessary to assume a strong influence on the measured variable $\Omega$ in particular caused by perfusion, as is shown as follows (or according to the article: IEEE Transactions on biomedical engineering, vol, 38 No. 12 December 1991: Simple Photon Diffusion Analysis of the Effects of Multiple Scattering on Pulse Oximetry by Joseph M. Schmitt):

If light beams are emitted by one transmitter (Page -1-; FIG. 1), wherein in this example 3 we have chosen light path representatives which together with the weight factors kn to be established later should characterise the light distribution in the tissue, then these light beams are attenuated when perfusion occurs through additional blood layers of different density (arterial blood which flows in additionally at a density $\delta$), if one assumes that the arterial pulsation is equal to zero, then the light intensity obtained in the receiver is:

$$I_{max} = I_1 + I_2 + I_3$$

If the arterial vessels now expand owing to new blood flowing in from the heart (the same naturally also applies for venous blood), then the density of the blood layer (and the light attenuation) increases for the individual beam paths and the following is obtained for the intensity received:

$$I_{min} = I'_1 + I'_2 + I'_3$$

wherein:

$$I'_1 = I_1 \cdot e^{-\alpha \cdot \delta 1}, \quad I'_2 = I_2 \cdot e^{-\alpha \cdot \delta 2}, \quad I'_3 = I_3$$

and $\alpha$:coefficient of extinction of the arterial blood

If the ratio is formed from $I_{min}$ and $I_{max}$, then the following is obtained:

$$\frac{I_{min}}{I_{max}} = \frac{I_1}{I_{max}} \cdot e^{-\alpha \cdot \delta 1} + \frac{I_2}{I_{max}} \cdot e^{-\alpha \cdot \delta 2} + \frac{I_3}{I_{max}}$$

or:

$$\frac{I_{min}}{I_{max}} \cdot k1 \cdot e^{-\alpha \cdot \delta 1} + k2 \cdot e^{-\alpha \cdot \delta 2} + k3, \quad k1 + k2 + k3 = 1$$

The coefficients kn characterise the scatter and light distribution in the tissue.

In order to determine the oxygen saturation it is necessary to use at least two wavelengths, whose coefficients of absorption differ from each other in dependence upon the level of oxygenation. In the case of increased absorption, the light portions which travel longer light path distances in the tissue are attenuated to a comparatively greater extent than the light portions which travel the shorter distances.

A similar situation is to be observed as the blood content in the tissue varies. If the blood content in the tissue varies, then light portions which travel a longer distance in the tissue are proportionately substantially more greatly attenuated than the light portions travelling the shorter distances. As a consequence, the middle distance along which the photons, which are registered in the receiver of the pulse oxymeter, travel is shortened as the blood content in the tissue increases.

In the assumption that light is scattered in the tissue, then it is possible using the above simple model and the following requirements:

1. Number of light path representatives $n \to \infty$;
2. Light path representatives kn are uniformly distributed to conclude that:

$$\Longrightarrow \frac{I_{min}}{I_{max}} = \frac{1 - e^{-\alpha \cdot \delta max}}{\alpha \cdot \delta max}$$

wherein $\delta_{max}$ represents a measurement for the perfusion p.

If this formula is used for two different measuring wavelengths in a calculation rule associated with the prior art for the measured variable $\Omega$, then a dependency of the oxygen saturation of arterial blood $SaO_2$ on the variable $\Omega$ and the perfusion p is obtained (see also FIG. 2):

$$\to SaO_2 = f(\Omega, p)$$

Similar influences can be caused by the pigmentation and pilosity of the skin in the case of pulse oxymeters whose light transmitter radiates by way of the skin into the tissue.

SUMMARY OF THE INVENTION

The technical problem resides in the fact that oxygen saturation of arterial blood must be determined in vivo using the process it pulse oxymetry without the perfusion in the tissue or pigmentation and pilosity of the skin influencing the measured result. It is therefore an object of the invention to locate from the number of possible calibration curves, those curves which render it possible to determine in the most precise manner the oxygen saturation of arterial blood.

To achieve this and other objects, the invention provides that by measuring the light attenuation LA in the tissue, which can be determined by virtue of taking a logarithm of the quotient of the intensity I registered in the sensor and the initial intensity $I_0$ at one wavelength. It is possible to select from a number of possible calibration curves those curves with which the oxygen saturation of the arterial blood can be determined in the most precise manner possible. Thus, the advantage of the invention resides in the fact that it is possible to improve considerably the accuracy of the measured values using pulse oxymeters particularly in cases where the oxygen saturation of the blood is low.

A further solution in accordance with the invention for the purpose of minimizing the error in the measure values resides in the fact that the measured value error can be minimized by weighting several measured value variables differently. In the case of measured variables which are obtained from different wavelength pairings the scatter pattern of the number of calibration curves associated therewith differs greatly in the case of different levels of oxygen saturation. The initial signal is obtained by the fact that once the measured value variable $\Omega n$ has been determined, then greater weighting is awarded those measured value variables at which the number of calibration curves demonstrate the least scatter.

A solution in accordance with the invention for the purpose of calibrating a pulse oxymeter utilises the injection of a medical dye which simulate changes in light absorption in the tissue owing to a change in the level of oxygen saturation without less oxygen actually being supplied to the tissue.

DESCRIPTION OF THE PREFERRED EMBODIMENTS

The invention is described with reference to several exemplified embodiments.

EXAMPLE 1

A pulse oxymetry sensor operates with the light wavelengths 660 nm, 805 nm and 940 nm.

In the case of the two wavelengths 660 nm and 940 nm the measured variable $\Omega$ is ascertained according to the following equation:

$$\Omega = \frac{\ln\left(\frac{I_{min}}{I_{max}}\right)_{660nm}}{\ln\left(\frac{I_{min}}{I_{max}}\right)_{940nm}}$$

For the two perfusions p1 and p2 calibration curves (see FIG. 2) are ascertained for the measured variable $\Omega$.

The amount of perfusion of the tissue is established from the strength of the light attenuation LA at 805 nm (isobestic point).

$$AL = -\ln\left(\frac{I_0 \cdot e^{-(\alpha \cdot \delta)}}{I_\Omega}\right) = \alpha \cdot \delta$$

where:

$\alpha \cdot \delta = (co \cdot \epsilon o - cr - \epsilon r) \cdot \delta$ (wherein:

$\delta$: Blood layer density or level of perfusion co, cr: Concentration of oxygenated and deoxygenated blood $\epsilon r$, $\epsilon r$ : Coefficient of extinction in the case of oxygenated and deoxygenated blood As in the present case the coefficient of extinction for oxygenated blood is identical to that of deoxygenated blood, the light attenuation AL1 in the case of perfusion p1 can be allocated directly to perfusion p1 and the light attenuation AL2 in the case of perfusion p2 directly to the perfusion p2.

Figure 1:
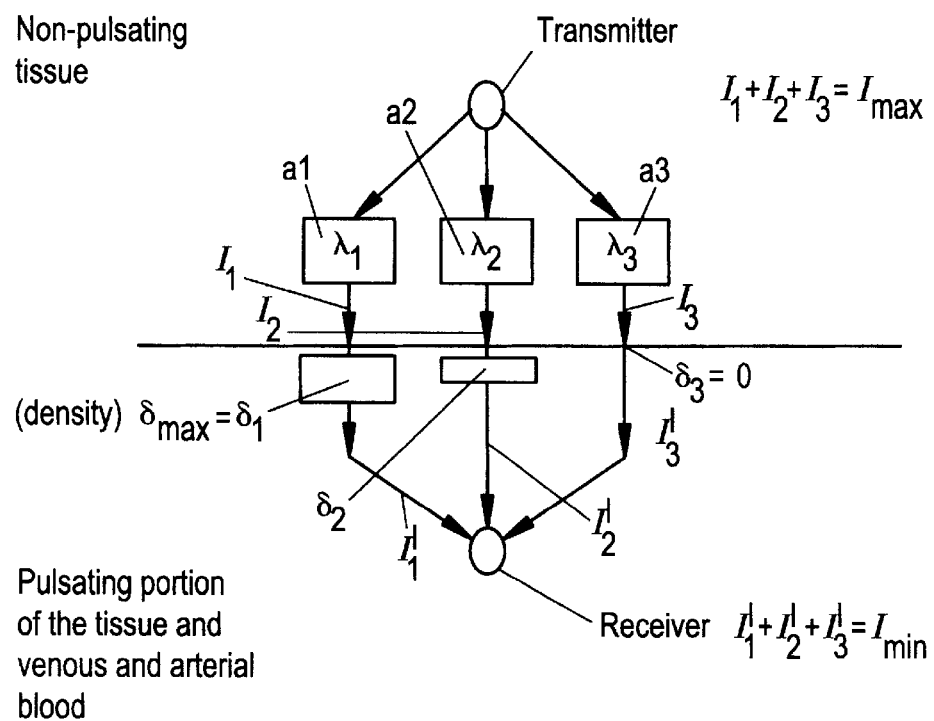
FIG. 1 is a schematic diagram of a pulse oximetry apparatus operating at three wavelengths $\lambda_1$, $\lambda_2$ and $\lambda_3$ from sources a1, a2 and a3.
Figure 2:
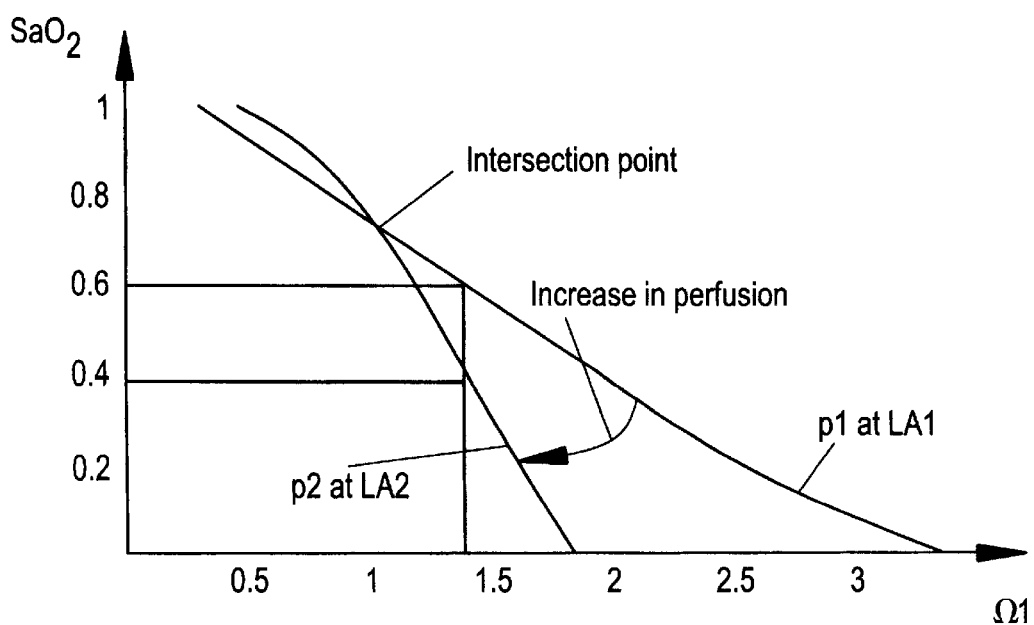
FIG. 2 is a graph of oxygen saturation of blood versus a measured oxygen saturation variable $\Omega 1$.

As shown in FIG. 2, in the case of the perfusion p1 an oxygen saturation $SaO_2$ of approx. 0.6 is obtained for $\Omega=1.5$, in contrast thereto in the case of perfusion p2 the $SaO_2$ amounts to only 0.38. By ascertaining in accordance with the invention the perfusion, it is therefore possible to avoid an error of 22% oxygen saturation.

The level of perfusion can also be ascertained in this case approximately by establishing the light attenuation AL at the wavelength 940 nm, since the influence of the oxygenation is low here in comparison to the perfusion, or by way of a weighting of the light attenuations over all three wavelengths.

EXAMPLE 2

In the case of a greater level of pigmentation and pilosity it is possible to determine the perfusion in the tissue by, for example, measurements being taken in the case of light wavelengths at two isobestic points (e.g. 560 nm and 850 nm). The following applies for light attenuation:

$LA_{560} = \delta_{Pig} \cdot \alpha_{Pig560} + \delta_{Blood} \cdot \alpha_{Blood560}$;

$LA_{805} = \delta_{Pig} \cdot \alpha_{Pig805} + \delta_{Blood} \cdot \alpha_{Blood805}$.

Since the coefficient of absorption a is known for the blood and the pigmentation and the pilosity, then the measurement for the blood layer density and perfusion $\delta_{Blood}$ can be ascertained from the light attenuations.

EXAMPLE 3

If the three light wavelengths 660 nm, 740 nm and 940 nm are used, then the following two measured variables are formed:

$$\Omega 1 = \frac{\ln\left(\frac{I_{min}}{I_{max}}\right)_{660nm}}{\ln\left(\frac{I_{min}}{I_{max}}\right)_{940nm}}$$

and $$\Omega 2 = \frac{\ln\left(\frac{I_{min}}{I_{max}}\right)_{740nm}}{\ln\left(\frac{I_{min}}{I_{max}}\right)_{940nm}}$$

Figure 3:
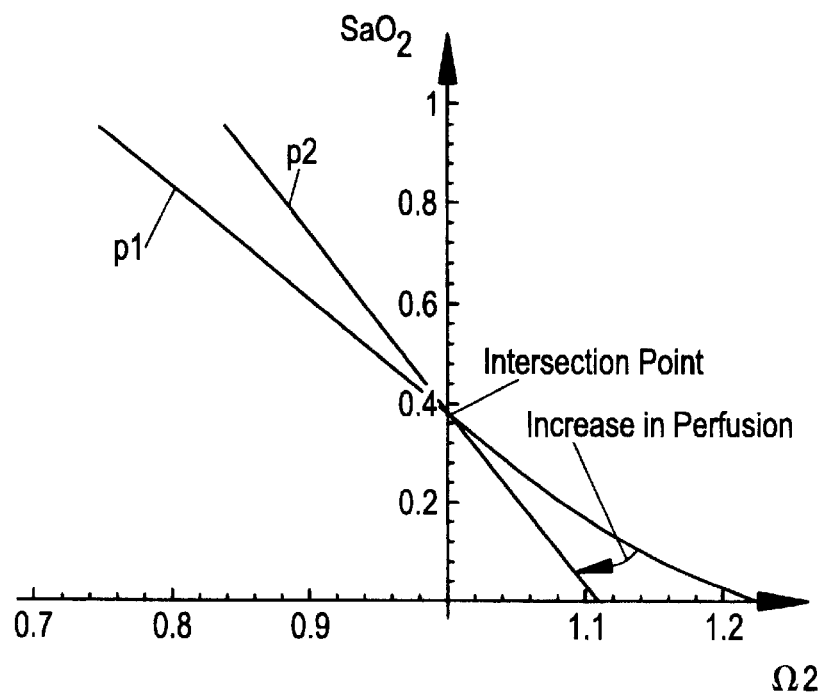
FIG. 3 is a graph of oxygen saturation of blood versus a measured oxygen saturation variable $\Omega 2$.
Figure 4:
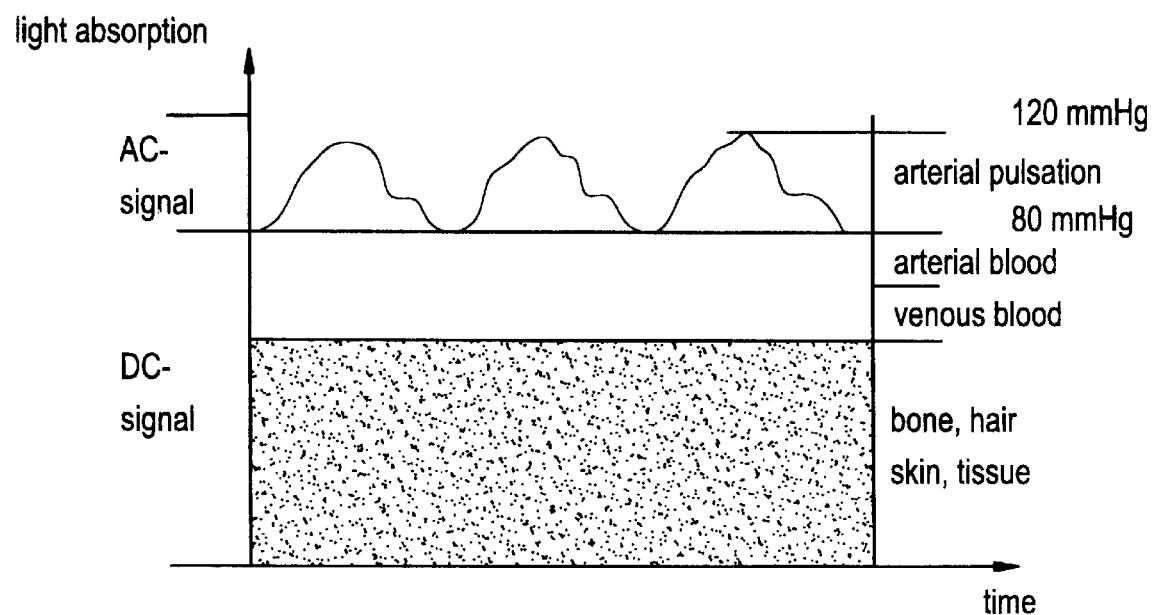
FIG. 4 is a diagram showing changes in light absorption over time.

If a value of 1 is obtained for a measurement for $\Omega 1$, then it can be assumed with a greater degree of accuracy that the oxygen saturation amounts to approximately 75% (as shown in FIG. 2), since the number of calibration curves intersect at this point. The intersection point of the number of curves for $\Omega 2$ lies likewise in the case of a value of approximately 1, however, here the oxygen saturation value amounts to approximately 40% (as shown in FIG. 3). Owing to the fact that in order to obtain an initial signal for the oxygen saturation in the case of high saturation values $\Omega 1$ is weighted more greatly than $\Omega 2$ and at low saturations $\Omega 2$ is weighted more greatly than $\Omega 1$, it is possible to increase the measuring accuracy using the pulse oxymetric measuring technique.

Note: The diagrams in FIG. 2 and FIG. 3 are only of qualitative importance. Deviations can occur if the geometry of the sensors is different.

EXAMPLE 4

It is difficult to calibrate a pulse oxymeter on human beings where the oxygen saturation is low, since low oxygen saturation is damaging for the tissue and a reduction in the saturation by, for example, binding an arm prevents the arterial pulsation which is necessary in order to carry out the pulse oxymetric measurement. It is possible to obviate this difficulty by injecting medical dyes in test probands. Methylene blue for example absorbs the light to a maximum at approximately 660 nm. Oxygenated blood absorbs light at 660 nm approximately ten times less than deoxygenated blood. Thus, it is possible by injecting methylene blue to simulate the deoxygenation of the blood at 660 nm. If as a second wavelength a transmitter is used having a light wavelength of 805 nm, a wavelength at which methylene blue absorbs hardly any light and the light absorption of the haemoglobin is not dependent upon the level of oxygenation, then calibration can take place—after taking blood samples from the tissue and carrying out a photometric analysis on said samples—over the entire oxygen saturation range. The influence of the haemoglobin content in the tissue on the calibration process can be determined, for example, by raising and lowering body parts and the resultant change in the blood in the tissue. The resultant change in perfusion is ascertained by virtue of determining the light attenuation LA through the tissue.

I claim:

1. Process for measuring oxygen saturation of arterial blood in tissue by pulse oxymetry, comprising the steps of directing electromagnetic radiation of at least two different wavelengths at the tissue, determining radiation retained by the tissue for each said wavelength, producing an electric signal (I1, I2, . . . ) corresponding to radiation intensity retained for each said wavelength, producing at least one measured oxygen saturation variable ($\Omega 1, \Omega 2 \ldots$), and compensation for undesired dependency of each individual measured variable on haemoglobin content in the tissue, pigmentation and pilosity of the skin, wherein for at least one wavelength a level of the measured light attenuation (LA) in the tissue is allocated to pilosity, pigmentation in the skin and haemoglobin content (perfusion p) of the tissue and the level of light attenuation (LA) is used as a correcting factor for one or several measured variables $\Omega n$, and wherein a value for the oxygen saturation of the arterial blood is obtained by selecting a calibration curve in dependence upon the LA from a number of possible calibration curves assigned by way of $\Omega n$ as an initial signal to one or several measured values for the measured variable $\Omega n$.

2. Process for measuring oxygen saturation of arterial blood in tissue by pulse oxymetry, comprising the steps of directing electromagnetic radiation of at least two different wavelengths at the tissue, determining the radiation retained by the tissue for each said wavelength, producing an electric signal (I1, I2, . . . ) corresponding to radiation intensity retained for each said wavelength, producing at least one measured oxygen saturation variable ($\Omega 1, \Omega 2, \ldots$), and compensating for undesired dependency of each individual measured variable on haemoglobin content in the tissue, pigmentation and pilosity of the skin, wherein a value for oxygen saturation of arterial blood is assigned as an initial signal to several measured variables ($\Omega 1, \Omega 2 \ldots$), which demonstrate a different dependency with respect to specific tissue relating characteristics, and wherein in each case the weighting on the measured variable $\Omega n$ is greater in order to form the initial signal, anticipated interference being less at the measured variable.

3. Process for measuring oxygen saturation of arterial blood in tissue pulse oximetry, comprising the steps of infecting a medical dye with which it is possible in the case of predetermined wavelengths to simulate different light absorptions based on levels of blood oxygenation in tissue intravenously into a human being or animal, taking blood samples from tissue of the human or animal during a period in which the dye decomposes and allocating to said blood samples based on absorption characteristics values for oxygen saturation of blood, assigning to a pulse oxymetry sensor initial signals corresponding to values of oxygen saturation of blood whilst simultaneously measuring the tissue with a pulse oxymetry sensor to determine light attenuation LA.

* * * * *

UNITED STATES PATENT AND TRADEMARK OFFICE
CERTIFICATE OF CORRECTION

PATENT NO. : 5,772,589
DATED : June 30, 1998
INVENTOR(S) : Peter Bernreuter

It is certified that error appears in the above-identified patent and that said Letters Patent is hereby corrected as shown below:

<u>Title page,</u>
After "Item [76] Inventor:" change the inventor information to read as follows:

-- Peter Bernreuter, Gartenstrasse 12, D-73230 Nabern Kirchheim, DE --;

Signed and Sealed this

Fourth Day of December, 2001

*Attest:*

*Nicholas P. Godici*

*Attesting Officer*

NICHOLAS P. GODICI
*Acting Director of the United States Patent and Trademark Office*